United States Patent [19]

Morris et al.

[11] 4,314,987

[45] Feb. 9, 1982

[54] METHOD FOR DIAGNOSING RHEUMATOLOGICAL DISEASES

[75] Inventors: Robert I. Morris; Allan L. Metzger; Arnold S. Weiss, all of Los Angeles, Calif.

[73] Assignee: Rheumatology Diagnostics Laboratory, Los Angeles, Calif.

[21] Appl. No.: 27,112

[22] Filed: Apr. 4, 1979

[51] Int. Cl.$^3$ ............................................. G01N 33/48
[52] U.S. Cl. ...................................... 424/1; 23/230 B; 424/12
[58] Field of Search ..................... 424/1, 12; 23/230 B

[56] References Cited

U.S. PATENT DOCUMENTS 3,897,212  7/1975  Leon et al. .

Primary Examiner—Deborah L. Kyle
Assistant Examiner—Christine M. Nucker
Attorney, Agent, or Firm—David O'Reilly; Donald M. Cislo

[57] ABSTRACT

A process for differential diagnosis of various rheumatological and arthritic diseases, all of which may yield similar antinuclear antibody test results. The process comprises a continuous sequence of tests on a single serum specimen to minimize and eliminate variations, thus providing accurate results. The process involves drawing a serum from a patient and first performing an antinuclear antibody test which is evaluated. If the evaluation is positive, then the particular type of positive indication is interpreted. If the interpretation reveals peripheral or speckled immunofluorescence, then a diagnosis of active Systemic Lupus Erythematosus (SLE), or mixed connective tissue disease (MCTD) are suggested, and automatically additional confirming tests will be performed as part of the process. These tests are the anti-DNA (Deoxyribonucleic Acid), the anti-ENA (extractable nuclear antigen). The test for the complement component C3 and a muscle disease test, called a creatine phosphokinase (CPK) which is a test for an enzyme contained in skeletal muscle. The results are compiled and reported in addition to reporting the degree of positivity by titer, which is the strength of a solution or the concentration of the antinuclear antibodies determined by a series of titrations or dilutions.

8 Claims, No Drawings

METHOD FOR DIAGNOSING RHEUMATOLOGICAL DISEASES

BACKGROUND OF THE INVENTION

This invention relates to a process for diagnosing diseases, and more particularly relates to a process for diagnosis of various rheumatological and arthritic disorders.

In testing for rheumatological and arthritic disorders, it is routine procedure for a physician to order an antinuclear antibody (ANA) test from a laboratory and receive a report on the results. The results are reported as positive and negative, along with the titer and the type of antinuclear antibody immunofluorescence pattern. The doctor was then left to his own devices as to how to interpret and treat the patient. Frequently, the doctor would order subsequent tests after a period of time because he was not sure of his diagnosis or the treatment that he began was not producing any results. These second tests usually occurred after a delay of weeks and sometimes months and would be performed on another serum speciman taken from the patient. Such delays in time and differences which can occur because of different serum specimens introduces numerous variations which could affect the accuracy and interpretation of subsequent tests. For example, there are statistical variations, laboratory variations, blood variations, or patient condition variations which can intervene, causing misinterpretation or errors in the testing results. These problems occur because the doctor does not realize immediately that the additional tests are necessary, or what tests are necessary and is operating on a somewhat trial-and-error procedure. The variations introduced because of delays cause considerable confusion and in many cases they order inappropriate laboratory tests based on the results received. The new diagnostic process disclosed herein eliminates the variations and solves a problem of inaccuracy and inappropriate testing.

SUMMARY OF THE INVENTION

The purpose of the present invention is to provide a process for differential diagnosis of rheumatological and arthritic diseases which is efficient and accurate.

The unique feature of the process of the present invention is in the recognition and interpretation of initial test results to detect the "road" signs pointing in the direction which one should go. That is, what additional tests are needed and when they should be performed. In the present invention the ANA test is performed as usual, and the immunofluorescent pattern interpreted. The ANA test is performed by reacting a sample of the patient's serum with a suitable substrate and then labelling or tagging the reactant fluorescent material. This produces a particular immunofluorescent pattern which must be properly interpreted. In some cases the ANA test proves negative and no further procedures need be performed. However, when the ANA test is positive, it is imperative that the results be properly interpreted. There are four types of positive indications. These are homogeneous, nucleolar, peripheral or speckled immunofluorescent patterns. In previous instances when these results are achieved, the particular immunofluorescent pattern, along with the titer, will be reported to the doctor. The doctor is then left to his own devices to determine the significance of the results.

However, it was recognized that when particular patterns are present that certain tests are definitely indicated and in order to get accurate results, these tests should be performed in a continuous sequence on the same serum sample. These particular patterns are the peripheral and speckled immunofluorescent patterns. In the homogeneous and nucleolar immunofluorescent patterns, they are distinct because in the first the immunofluorescent is uniform, while in the latter, the nuclei will fluoresce in localized areas. In the peripheral or rim pattern, the immunofluorescent pattern is apparent around the rim of the nucleus. The speckled pattern is a uniform speckled appearance over the entire nuclei. It was recognized that in the latter two cases certain tests are indicated and should be performed in a continuous sequence of the same blood sample or serum and not separate tests spaced apart at separate times as the procedure now is.

Through experimentation is was recognized that the rim or peripheral pattern consistently indicated a possible diagnosis of active SLE and infrequently other diseases. The next step in the process then was logically the test for confirmation of the active SLE, such as the anti-DNA antibody test and the complement C3 antigen test. These tests also should be performed in a continuous sequence on the same serum or blood sample from a patient.

Likewise, through experimentation, it was found that the speckled pattern consistently indicated mixed connective tissue disease (MCTD) and much less frequently Lupus or other rheumatological disorders. Thus, the next logical step in the process after this interpretation is to perform the anti-ENA (extractable nuclear antigen) antibody test and the muscle disease test for skeletal muscle enzymes called CPK (creatine phosphokinase).

It is one object of the present invention to provide a process for differential diagnosis of various rheumatological disorders, comprised of a continuous sequence of tests on a single blood serum sample.

Another object of the present invention is to provide a process for differential diagnosis of various rheumatological disorders, including recognition and evaluation of certain immunofluorescent patterns and performing in continuing sequence the tests required for confirmation of particular diseases.

Still another object of the present invention is to provide a process for differential diagnosis of various rheumatological disorders which confirms the diagnosis of a rim or peripheral pattern by continuous sequence performance of anti-DNA and complement C3 tests.

Still another object of the present invention is to provide a process for differential diagnosis of various rheumatological disorders by recognizing the indication of a particular diagnosis of a disease from a speckled immunofluorescent pattern and a continuous testing for confirmation of the disease by performing anti-ENA and CPK tests.

DETAILED DESCRIPTION OF THE PREFERRED EMBODIMENT

This invention is a process for diagnosing rheumatological disorders which recognizes the importance of proper interpretation of the results of each test and recognizing the direction or sequence for performing subsequent tests. It is also a unique process in that it is performed in a continuous sequence over a period of time on the same blood serum or sample in order to assure accurate results. It was found important to perform the test in a continuous sequence because unnecessary tests may be eliminated and the disease may become inactive after a period of time.

In testing for and recognizing various rheumatological disorders, the first step is to obtain a blood sample from the patient and perform certain laboratory tests. The blood speciman or sample is first processed by centrifuging and separating the serum. Subsequently the ANA test is performed on a serum sample. If the ANA test is negative, no further laboratory test is done as Lupus or mixed connective tissue diseases are contraindicated. If the results are positive, then the results must be interpreted.

The ANA test is a laboratory procedure for detecting human antinuclear antibodies by indirect immunofluorescence. This method is composed of two antigen-antibody reactions. The first reaction takes place between the human serum sample containing certain antibodies and an antigen which is localized in an appropriate substrate section. The second reaction is between the complex of the auto-antibody and its specific antigen and the antihuman specific antibody which has been labelled or tagged with fluorescene isothiocyanate. The fluorescence is then viewed through an ultraviolet fluorescent miscroscope to determine the immunofluorescent pattern. The various patterns which can be preceived are the homogeneous pattern, a peripheral or rim pattern, a speckled pattern, a nucleolar pattern, or a mixed pattern. The homogeneous, nucleolar and mixed are non-specific in that a number of diseases could be indicated, giving rather indefinite results.

However, it was recognized, after much experimentation, that the peripheral or rim pattern and speckled pattern do consistently indicate a particular type of disease. In the case of the peripheral or rim pattern, the disease indicated is active Systemic Lupus Erythematosus (SLE), for which there are certain other confirming tests. It was now discovered that in order to pin down the confirmation by these tests, that it should be performed as a continuous sequence of tests in time on the same blood serum sample in order to avoid the numerous errors which could be introduced by delays in time, differences of blood samples, etc. Thus, once this particular interpretation is made, confirming anti-DNA and complement C3 tests are performed on the same blood sample in a continuous time sequence to confirm the diagnosis. This is because, as the process reveals, the patterns themselves are not diagnostic. The patterns only suggest certain directions or routes for subsequent tests, but as was previously discussed, these tests would be delayed in time and performed on different samples introducing a multitude of variations, causing error in the interpretation.

The anti-DNA test is a test for particular antibodies utilizing a radioactive compound, usually iodine and reading the results on a radioactive counter and in particular a gamma counter.

The peripheral or rim pattern also, because it consistently suggests the disease named hereinabove, indicates that a human complement $C_3$ test should be performed. The principle of this test is a radial immunodiffusion for complement $C_3$ determination involving diffusion of an antigen (complement $C_3$) through a semi-solid medium containing an antibody (anti-$C_3$) resulting in the formation of a circular zone of precipitation. The diameter of the zone is measured and is a function of the concentration of the diffusing antigen's complement component $C_3$. In the tests an antibody is placed in a semi-solid media which has wells cut into it. The patient's serum is put into the wells and diffuses out in all directions. When the antibody in the media reacts with the specific antigen complement $C_3$ that we are looking for in the patient's serum, a chalky-colored precipitate forms and is measured after a certain period of time. The particular method of performing and measuring the complement $C_3$ test is known in the art.

When a speckled pattern is perceived after the concentration from the ANA test, it has been consistently found that mixed connective tissue disease (MCTD) is indicated (i.e. "specific" for MCTD). There may be other diseases indicated or associated with this pattern, such as SLE, but the results are not "specific". The recognition that this pattern is specific (i.e. consistent) for mixed connective tissue disease means that confirming tests, such as anti-ENA and muscle disease tests (CPK) should be performed. Again, in order to eliminate variations due to differences in time causing a change in results, it was found important to perform these tests in a continuous time sequence on the same blood sample. The anti-ENA test in principle is a test for detecting and identifying certain soluble nucleoproteins in the sera of patients and in particular the antibodies to the SM (Smith-antigen) and the RNP (ribonucleoprotein) antigen.

The anti-ENA test involves a double diffusion technique to determine antibodies to the SM and RNP antigens. Frequently with skeletal muscle diseases the enzyme creatine phosphokinase can be found and therefore the CPK test should also be performed as part of the process for the mixed connective tissue disease. The measure of CPK activity in the patient'serum is a kinetic determination using ultraviolet UV photometry. The enzyme CPK activity is greatest in striated muscle, brain and heart tissue respectively. Thus, the determination of CPK activity has proven to be a tool more sensitive than many other laboratory tests in investigation of skeletal muscle disease, including cardiovascular diseases.

Thus, there has been disclosed a unique process for differential diagnosis of rheumatological and arthritic diseases which recognizes the need for certain tests in a continuous sequence of a single patient sample. Although certain tests have been somewhat briefly described, the methods of performing these tests vary widely and no particular rigid adherence to one form of a test is contemplated. For example, the anti-DNA test can be performed by the Farr technique, but there are other techniques which may be equally acceptable. The same applies to other tests described or suggested in the differential diagnosis process described herein.

Obviously, many modifications and variations of the present invention are possible in light of the above teachings, and it is therefore to be understood that the full scope of the invention is not limited to the details disclosed herein, but may be practiced otherwise than as specifically described.

What is claimed is:

1. A process for differential diagnosis of rheumatological diseases comprising:
   drawing a blood specimen;
   separating the serum to be tested from the blood specimen;
   reacting the serum with an antigen to produce antinuclear antibodies;
   labelling the antinuclear antibodies with a fluorescent material;

determining whether the antinuclear antibody labelling for a positive immunofluorescent pattern has produced a homogeneous pattern, rim pattern, speckled pattern or nucleolar pattern;

testing the same serum separated from the blood specimen in a continuous sequence for Systemic Lupus Erythematosus or Mixed Connective Tissue Disease if the pattern is a rim pattern or speckled pattern, respectively.

2. The process according to claim 1 including:

diluting the serum to determine titer if one of the positive immunofluorescent patterns is discovered.

3. The process according to claim 1 wherein a rim pattern is discovered including the steps of, reacting the serum sample with DNA labelled with a tracer element, such as radioactive iodine;

counting the labelled serum with a radioactive counter to determine if anti-DNA antibodies are present.

4. The process according to claim 3 including the further step of testing the serum for complement component $C_3$ antigen.

5. The process according to claim 4 wherein the human complement of $C_3$ test includes the steps of preparing a semi-solid medium having anti-complement $C_3$ antibody;

forming wells in said semi-solid body;

filling said wells with serum samples;

measuring the circular zone of precipitation to determine the diffusing antigen complement $C_3$ concentration.

6. The process according to claim 1 wherein a specified pattern is discovered including the step of testing the serum for anti-extractable nuclear antigens.

7. The process according to claim 6 including the steps of reacting the serum sample with a source of soluble nuclear proteins;

reacting the first reactant with a source of SM and RNP antigens to detect the presence of either or both SM or RNP antibodies.

8. The process according to claim 6 including the step of testing the serum sample for creatine phosphokinase enzyme.

* * * * *